United States Patent [19]

Shenvi

[11] Patent Number: 4,537,773

[45] Date of Patent: Aug. 27, 1985

[54] α-AMINOBORONIC ACID DERIVATIVES

[75] Inventor: Ashokkumar B. Shenvi, Wilmington, Del.

[73] Assignee: E. I. Du Pont de Nemours and Company, Wilmington, Del.

[21] Appl. No.: 558,361

[22] Filed: Dec. 5, 1983

[51] Int. Cl.$^3$ .............................. C07F 5/02; C07F 5/04; C07F 7/08; C07F 7/02
[52] U.S. Cl. ......................................... 514/63; 514/64; 556/403; 568/6; 260/462 C
[58] Field of Search ........................... 556/403; 568/6; 260/462 C; 424/185, 184

[56] References Cited

U.S. PATENT DOCUMENTS

| | | | |
|---|---|---|---|
| 3,069,454 | 12/1962 | Willcockson et al. | 260/462 C |
| 3,131,208 | 4/1964 | Woods | 260/462 C |
| 3,222,379 | 12/1965 | Farthouat | 260/462 C X |
| 3,317,580 | 5/1967 | Hillman | 568/6 X |

Primary Examiner—Paul F. Shaver

[57] ABSTRACT

α-Aminoboronic acids and derivatives of formula

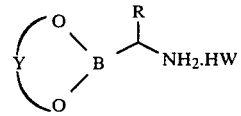

are potent, reversible inhibitors of aminopeptidases.

22 Claims, No Drawings

α-AMINOBORONIC ACID DERIVATIVES

BACKGROUND OF THE INVENTION

This invention relates to boron equivalents of aliphatic and aromatic amino acids, which equivalents are potent, reversible inhibitors of certain proteolytic enzymes.

A variety of organoboron compounds in general, and of boronic acids in particular, are known. Muetterties. E. L., Ed., *The Chemistry of Boron and Its Compounds,* (Wiley, New York, 1967) pp. 443–615; Steinberg, H., Ed., *Organoboron Chemistry,* (Interscience, New York, 1964) Vols. 1 and 2; and Gerrard, W. *The Organic Chemistry of Boron,* (Academic Press, New York, 1961) are useful background references in the general field of the present invention.

Several references report the synthesis of alkyl, aralkyl and arylboronic acids, which were observed to be inhibitors of a class of proteolytic enzymes known as serine proteases. Proteases, which cleave proteins at single, specific, peptide bonds, have been classified mechanistically into four groups: serine, thiol or cysteinyl, acid, and metallo proteases, according to Cuypers, et al., *J. Biol. Chem.* 257:7086 (1982), and certain references cited therein.

Rawn, et al., *Biochemistry* 13:3124 (1974), and Koehler, et al., *Biochemistry* 10:2477 (1971) disclose use of 2-phenylethaneboronic acid as an inhibitor of chymotrypsin, a serine protease. Inhibition of a bacterial serine protease, subtilisin, by 2-phenylethaneboronic acid, benzeneboronic acid, and methaneboronic acid is described by Lindquist, et al., *Arch. Biochem. Biophys.* 160:135 (1974). Beesley et al., *Biochem J., Molecular Aspects* 209:229 (1983), disclose inhibition of class C β-lactamases, also classified as serine proteases, by certain arylboronic acids.

A limited number of aminoboronic acids, or aminoboronic acid esters in protected form, have been reported in the chemical literature. Lindquist et al., *J. Am. Chem. Soc.* 99:6435 (1977) describe synthesis of N-benzylaminomethaneboronic acid I,

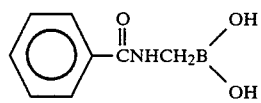

as well as its use as an inhibitor of α-chymotrypsin. However, Matteson et al., *J. Am. Chem. Soc.* 103:5241 (1981) suggest that the compound actually obtained by Lindquist, et al., was more likely an isomer, the imido ester II

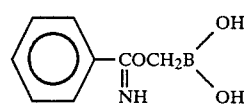

rather than an α-aminoboronic acid. Matteson, et al., also report synthesis of the following amino- and acetamidoboronic acids:

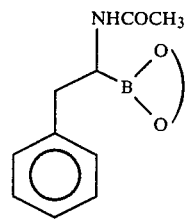

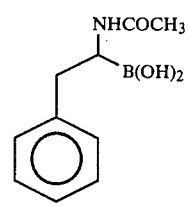

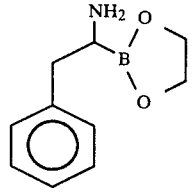

The oxygen atoms of formula III, above, are linked by a pinane or ethylene bridge. Acetamide derivatives IV and V were observed to inhibit α-chymotrypsin. Philipp, et al., *FEBS Letters* 133:36 (1971), report that compound IV also inhibited subtilisin. Isolation of amine salts was not reported. A critical intermediate in the synthesis of the foregoing compounds was the disilane derivative VI;

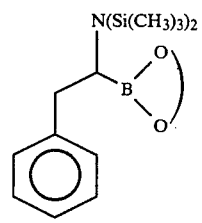

which was prepared by treatment of an analogous α-chloro compound with lithiohexamethyldisilazane.

Homologation of pinacol and ethylene glycol esters of boronic acids with (dichloromethyl)lithium, providing corresponding α-chloro compounds, is described by Matteson et al., *J. Am. Chem. Soc.* 102:7588 (1980). Transesterification of pinanediol esters to diethanolamine esters of α-chloroboronic acids is disclosed by Matteson, et al., *J. Am. Chem. Soc.* 102:7590 (1980).

G. E. Lienhard, in Sandler M., ed., *Enzyme Inhibitors as Drugs* (University Park Press, Baltimore, 1980), pp. 43–51, has speculated that boronic acid analogues of amino acids and small peptides should represent "extremely potent inhibitors" of serine and cysteine (thiol) proteases. Lienhard suggests that the mechanism of inhibition of such proteases by boronic acids involves formation of a stable complex between inhibitor and enzyme active site, which complex structurally resembles the transition state for the reaction catalyzed by the enzyme.

Leucine aminopeptidase (LAP) is an aminopeptidase classified as a metalloenzyme, which catalyzes hydrolysis of peptides at the carboxyl terminus of leucine residues. Elevated levels of LAP are frequently observed in patients with hepatobiliary disease.

Known inhibitors of LAP include chloromethyl ketone analogs of amino acids (Birch, et al., *Arch. Biochem. Biophys.* 148:447 (1972)); bestatin, a short peptide (Umezawa, et al., *J. Antibiotic* 29:857 (1976)), o-, m-, and p-leucylanilides (Taylor, et al., *Arch. Biochem Biophys.* 210:90 (1981)); amino acid hydroxamates (Chan. et al., *J. Biol. Chem.* 257:7955 (1982)); and α-amino aldehydes (Anderson, et al., *Biochemistry* 21:4177 (1982)).

Colletti-Proviero, et al., *Biochem. Biophys. Acta* 657:122 (1981); *Neuropeptides* 2:31 (1981); and *Biochem Biophys. Res. Comm.* 107:465 (1982) describe properties of human enkephalin-degrading enzyme (HEDA) which, like LAP, is an aminopeptidase and a metalloenzyme.

A considerable body of evidence suggests that leu-enkephalin and met-enkephalin, pentapeptides which are collectively known as enkephalins, exert a profound analgesic activity in the body, and that enzymes such as HEDA play a role in enkephalin inactivation and resulting loss of analgesia. For example, U.S. Pat. No. 4,380,535 discloses a method of enhancing and prolonging enkephalin-induced analgesia by administration of enzyme inhibitors. Davis, et al., *Fed. Proc.* 42:1476 (1983) describe experiments in which analgesia elicited by exogenously administered leu-enkephalin was enhanced by administration of such compounds as leucinal, which inhibits aminopeptidase activity. Thus, new compounds with specific HEDA-inhibiting activity are of considerable interest as potential therapeutic agents.

SUMMARY OF THE INVENTION

The present invention provides compounds of formula

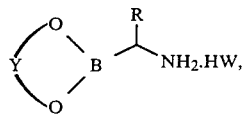

wherein
R is alkyl or $-CH_2R^1$;
$R^1$ is $-XR^2$, aryl, or aryl substituted with one or more alkyl groups;
$R^2$ is $-H$, alkyl, or $-SiR^3R^4R^5$;
$R^3$, $R^4$ and $R^5$ are independently alkyl, aryl or aryl substituted with one or more alkoxy groups;
X is O or S;
Y is a moiety derived from a dihydroxy compound comprising at least two hydroxy groups separated by at least two connecting atoms in a chain or ring, said chain or ring comprising carbon atoms and, optionally, a heteroatom which can be N, S, or O; and
HW is a mineral acid, sulfonic acid, alkanoic acid or a perfluoroalkanoic acid.

The invention also comprehends free amines of formula

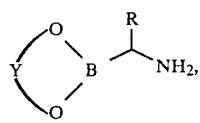

wherein
R and Y are as previously defined, provided that where Y is $-CH_2CH_2-$, R cannot be

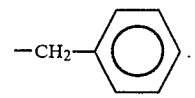

In addition, three classes of intermediates to the foregoing classes of compounds are provided, a first class having the formula

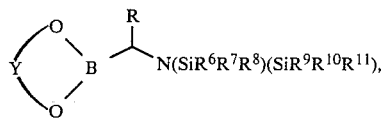

wherein
R and Y are as previously defined, and
$R^6$ through $R^{11}$ are independently alkyl, aralkyl, aryl, or substituted aryl, provided that aryl substituents do not contain active hydrogen, and provided that, where $R^6$ through $R^{11}$ are $-CH_3$ and Y is $-CH_2CH_2-$ or

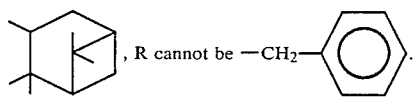

A second class of intermediates includes compounds of formula

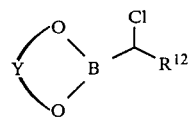

wherein
$R^{12}$ is lower alkyl or benzyl and Y is as previously defined; provided that, where Y is $-CH_2CH_2-$ or

$R^{12}$ cannot be benzyl.

A third class of intermediates includes compounds of formula

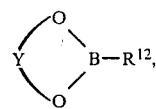

wherein
$R^{12}$ and Y are as previously defined.

DETAILED DESCRIPTION OF THE INVENTION

The principal class of compounds provided by the present invention are salts of protected esters of α-aminoboronic acids of the formula

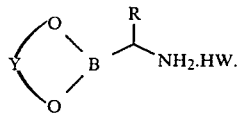

The identity of acid moiety HW and protective group Y can vary widely within the context of the invention. Suitable values for HW include mineral acids, for example, HCl, HBr, HI, HNO$_3$, H$_2$SO$_4$ or H$_3$PO$_4$; sulfonic acids R'SO$_3$H, where R' is lower alkyl, aralkyl, aryl or alkaryl, for example, benzenesulfonic acid, methylsulfonic acid, or dimethylbenzylsulfonic acid; and alkanoic or perfluoroalkanoic acids R"CO$_2$H, where R" is alkyl, perfluoroalkyl, aryl, alkaryl, or aralkyl, for example, acetic acid, perfluoroacetic acid, formic acid, isobutyric acid, dimethylacetic acid, benzoic acid, phenylacetic acid, and other equivalents apparent to those of skill in the art.

Suitable values for protective group Y include moieties derived from compounds containing at least two hydroxy groups separated by at least two connecting atoms in a chain or ring. Exemplary compounds within the foregoing definition include, for example, pinacol, perfluoropinacol, pinanediol, ethylene glycol, diethylene glycol, catechol, 1,2-cyclohexanediol, 1,3-propanediol, 2,3-butanediol, 1,4-butanediol, glycerol, diethanolamine, and other equivalents.

"Alkyl," as used throughout the specification, refers to aliphatic groups, straight or branched-chain, having one to ten carbon atoms. "Lower alkyl" refers to aliphatic groups, straight or branched-chain, having one to four carbon atoms. "Perfluoroalkyl" refers to alkyl where all hydrogens are replaced with fluorine atoms. "Aryl" means a radical derived from an aromatic hydrocarbon, i.e., phenyl. "Aralkyl" means an alkyl radical substituted with an aryl moiety, e.g., phenethyl. "Alkaryl" means an aryl radical substituted with one or more alkyl groups, e.g., tolyl. "Alkoxy" means an alkyl radical linked by an oxygen atom to another atom or group. "Substituted aryl," in the context of the present invention, means aryl substituted with one or more substituents not having active hydrogen, e.g., lower alkyl, lower alkoxy, halo, nitro, and sulfato.

Contemplated classes of compounds within the scope of the present invention include the following. A first class includes compounds wherein R is alkyl or —CH$_2$R$^1$ where R$^1$ is aryl or aryl substituted with one to four alkoxy groups. Principal subclasses within this class are a subclass including compounds where R is lower alkyl, and a subclass including compounds where R is —CH$_2$R$^1$, and R$^1$ is aryl or aryl substituted with one, two, or three lower alkoxy groups.

A second class includes compounds where R is —CH$_2$R$^1$ and R$^1$ is —XR$^2$, where X is S or O and R$^2$ is —H, alkyl, or —SiR$^3$R$^4$R$^5$. Principal subclasses within the second class include compounds where X is O and R$^2$ is lower alkyl; compounds where X is O and R$^2$ is SiR$^3$R$^4$R$^5$; and compounds where X is S and R$^2$ is lower alkyl.

The free amines of the invention are compounds of formula

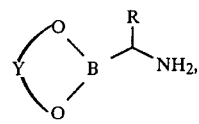

where R and Y are as previously defined. Excluded, however, from the present invention, is the free amine compound in which R is benzyl and Y is —CH$_2$CH$_2$—. Contemplated classes of free amine compounds within the scope of the invention include classes and subclasses corresponding in scope to the classes identified for the salts of protected esters of α-aminoboronic acids discussed above.

The present invention further comprehends three classes of critical intermediates to the foregoing salts and free amines. The first intermediates class includes compounds of formula

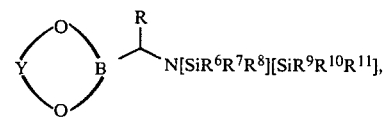

wherein R and Y are as defined previously, and R$^6$ through R$^{11}$ are independently alkyl, aralkyl, aryl, or substituted aryl. Groups having active hydrogen, which are excluded from those groups defined as "substituted aryl," include, for example, hydroxy, amino, and sulfhydryl. Excluded from the scope of the first intermediates class are compounds in which R is benzyl, R$^6$ through R$^{11}$ are each methyl, and Y is —CH$_2$CH$_2$— or

The second class of intermediates of the invention include compounds of formula

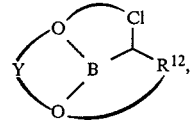

where R$^{12}$ is lower alkyl or benzyl and Y is as previously defined; provided that, where Y is —CH$_2$CH$_2$— or

R$^{12}$ cannot be benzyl.

The third class of intermediates includes compounds of formula

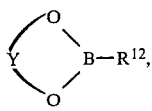

where

R[12] and Y are as previously defined.

The various compounds of the present invention can be made according to the following synthetic scheme, which is detailed both generically and by specific examples included herein.

SYNTHESIS

The compounds of the present invention are prepared by a synthesis generally similar to that disclosed by Matteson, et al., *J. Am. Chem. Soc.* 105:5241 (1981).

Step A: Grignard Reaction

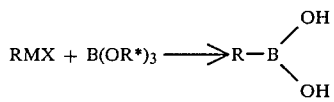

This reaction step is conducted by treating an alkyllithium, aryllithium, alkaryllithium, aralkyllithium, alkylmagnesium, arylmagnesium, alkarylmagnesium or aralkylmagnesium halide Grignard reagent (RMX) with one equivalent of a trialkylborate (B(OR*)$_3$), preferably triethylborate, forming a boronic acid 1. The organometal halide Grignard reagent can be prepared by treating an alkyl, aryl, aralkyl or alkaryl halide with Li or Mg in a suitable solvent, e.g., ether or tetrahydrofuran, or obtained from commercial sources. R, in the formula above, is as previously defined, except R$^2$ is not —H. Substituents having active hydrogen are to be excluded.

The reaction of triethylborate and Grignard reagent is conducted at about −72° C. by simultaneous addition of these two reagents to a flask containing ether at about −72° C. Other solvents, e.g., tetrahydrofuran or other alkyl ethers, can be used instead of ether. This procedure is generally similar to that described in N. Rabjohn, Ed., *Organic Synthesis,* (Wiley, New York, 1963) Coll. Vol. IV, p. 68–72.

Step B: Esterification

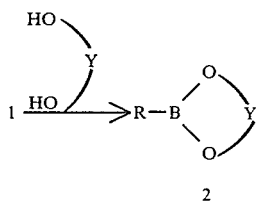

Boronic acid 1, prepared in Step A, can be isolated for esterification, or, in the alternative, employed without isolation. Esterification is conducted by treating boronic acid 1, dissolved in ether or other inert solvent, with one or more equivalents of pinacol or other dihydroxy compound (Y(OH)$_2$) selected from the group previously described. This reaction can be conducted at ambient temperature for 1 to 16 hours.

Step C: Homologation

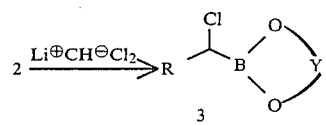

Boronic ester 2, prepared in step B, is homologated by treatment with about one equivalent of (dichloromethyl)lithium, or, optionally, (dibromomethyl)lithium, at about −72° C. in dimethoxyethane, tetrahydrofuran, an alkyl ether, or other suitable solvent. (Dichloromethyl)lithium can be generated by treatment of dichloromethane with lithium diisopropylamide, or other suitable amide, e.g., sodium dialkylamide. Lithium diisopropylamide is prepared by treating diisopropylamine with n-butyllithium in hexane in the presence of small amounts (ca 1%) of tetrahydrofuran. Other amides are prepared by treatment of corresponding secondary amines with an alkyl metal or metal hydride in a suitable solvent. Step C will not proceed using compounds 2 which contain a reactive hydrogen, for example, where Y is —(CH$_2$)$_2$NH(CH$_2$)$_2$—, without first blocking or protecting the reactive hydrogen. This homologation step is described by Matteson, et al., *J. Am. Chem. Soc.* 102:7588 (1980).

Step D: Displacement of chloride with lithiohexamethyldisilazane

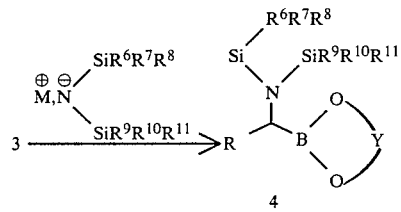

This reaction involves treating α-chloroboronic ester 3 with an equivalent of lithiohexamethyldisilizane in tetrahydrofuran at −72° C., followed by stirring the resulting reaction mixture for about 16 h to about 7 days at ambient temperatures. Other metals can be used in place of lithium, and other solvents such as alkyl ethers, and higher temperatures, e.g., 0°–100° C., can be employed. Lithiohexamethyldisilazane is prepared by treating the corresponding amine, hexamethyldisilazane, with n-butyllithium in tetrahydrofuran at about 0° C. Other disilazanes can be prepared by treating corresponding amines with either an alkyl metal or a metal hydride in an inert solvent at about 0° C. to about 23° C. A substantially similar procedure has been described by Matteson, et al., *J. Am. Chem. Soc.* 103:5241 (1981).

Step E: Desilylation

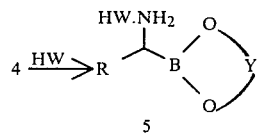

This reaction comprises treating silylated compound 4 with three equivalents of trifluoroacetic acid in ether at about 0° C. Other proton sources, e.g., alcohols, mineral acids and alkanoic acids, can be used, and other inert solvents can be employed in place of ether. Temperatures from about −72° C. to about 23° C. are suitable. The salt of the ester crystallizes from the reaction mixture. Related desilylations are described in J. F. W. McOmie, Ed., *Protective Groups in Organic Chemistry* (Plenum, New York, 1973).

Step F: Conversion of salt to free amine

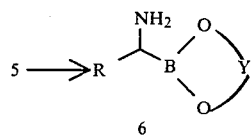

Free amine 6 can be prepared from salt 5 by treatment with a base, e.g., alkali metal or alkaline earth metal carbonates or hydroxides, in aqueous solutions of organic/aqueous mixtures, e.g., ethanol/water, methanol/water, or other equivalents.

Compounds 5 or 6, where $R^2=H$, are prepared by dealkylation or desilylation of 5 or 6 where $R^2=C_1-C_{10}$ alkyl or $-SiR^2R^3R^4$.

Esters 5 and 6 can also be modified by conversion to other esters through transesterification, e.g., transesterification of a pinacol ester to a pinanediol ester.

Conversion of the salt to the free amine and transesterification are described in general for nonboronic compounds in texts such as March, *Advanced Organic Chemistry*, (McGraw-Hill, New York, 1968) and Hilgetag and Martini, Eds., *Preparative Organic Chemistry*, (Wiley, New York, 1972).

Similar reactions for various boron-containing compounds are described in Steinberg, Ed., *Organoboron Chemistry* (Interscience, New York, 1964) and by Matteson et al., *J. Am. Chem. Soc.* 102:7590 (1980).

UTILITY

Compounds 5 and 6 of the present invention are potent inhibitors of aminopeptidases in general, specifically leucine aminopeptidase (LAP) and human or mammalian enkephalin-degrading aminopeptidase (HEDA).

As specific LAP inhibitors, the compounds of the invention can be utilized for direct determination of LAP levels in serum samples. Elevated LAP levels are clinically associated with hepatobiliary disease, including hapatitis, cirrhosis, obstructive jaundice and metastatic liver carcinoma. A more detailed discussion of the clinical diagnostic implications of LAP levels is provided by Henry et al., *Clinical Chemistry*, (Harper and Row, New York, 1974) pp. 952-954; and Henry et al., *Clinical Diagnosis and Management by Laboratory Methods*, Vol. 1 (W. B. Saunders, Philadelphia, 1979) pp. 360-361, 374-376.

In addition, the compounds of the invention can be employed as test reagents for determining the active site concentration of commercially-available LAP, which is provided as a test kit reagent and standard for clinical LAP determinations.

Compounds 5 and 6 of the invention can be administered to mammals at dosage rates between 0.2 and 200 mg/kg, to potentiate natural or exogeneously induced enkephalin analgesia, by inhibiting the leu-enkephalin degrading activity of human or mammalian enkephalin-degrading aminopeptidases.

Compounds 5 and 6 can be administered alone, in combination with one another, or in combination with inert pharmaceutically acceptable carriers in a variety of dosage forms, orally or parenterally. Dosage requirements will vary with the severity of the pain, the animal being treated, the compound employed and the dosage form employed. Therapy is instituted at low dosages and the dosage is increased incrementally until a desired effect is achieved.

For unit dosages, the active compound can be compounded into any of the usual oral or parenteral dosage forms, including tablets, capsules, elixir, or suspensions. The dosage forms can contain conventional inert pharmaceutical carriers to serve as diluents, lubricating agents, stabilizing agents, preserving agents, or flavoring agents, as needed. Suitable pharmaceutical carrying agents and methods of preparation thereof will be apparent to those skilled in the art. In all cases, proportions of active ingredient in a dosage form must be sufficient to impart analgesic activity thereto.

Finally, intermediates 2, 3 and 4 are useful in synthesizing product compounds 5 and 6 of the invention. Moreover, certain intermediates 2 and 3, identified as the second and third classes of intermediates above, are useful agricultural chemicals for control of certain ant, mite, leafhopper, bollworm, and bean aphid species.

Overall, product compounds 5 of the invention are preferred on the basis of cost, ease of handling and storage, and inhibitory capacity against LAP and HEDA. Preferred values of R are $-CH_3$, $-CH(CH_3)_2$, $-CH_2CH_2(CH_3)_2$, $-CH(CH_3)C_2H_5$, and $-CH_2C_6H_5$ (benzyl). Preferred values of Y are

$-(CH_2)_2-NH-(CH_2)_2-$. Preferred values of HW are $CF_3CO_2H$, $CH_3CO_2H$, HCl, and HBr.

The most preferred compounds of the invention are the compounds 5, where R is $-CH(CH_3)C_2H_5$ or $-CH_2C_6H_5$ (benzyl); Y is

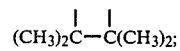

and HW is $CF_3CO_2H$, due to superior capacity for inhibition of LAP; and the compounds 5 where R is $-CH_2C_6H_5$ (benzyl) or $-CH_2CH(CH_3)_2$, Y is

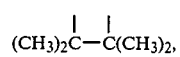

and HW is $CF_3CO_2H$, due to superior capacity for inhibition of HEDA.

Methods of preparing illustrative compounds within the scope of the present invention are detailed in Examples 1-25. In Examples 1-21, which are summarized in Table 1, below, protecting group Y was derived from pinacol hexahydrate. In Examples 22-25, protecting group Y was derived from 1,3-propanediol. Examples 26-30 illustrate use of compounds 5 of the invention in experiments involving inhibition and titration of certain aminopeptidases. In the following examples, all melting points are uncorrected, and all temperatures are reported in degrees Celsius (°C.). Proton nuclear magnetic resonance ($^1$H NMR) chemical shifts are reported in δ units downfield from an internal tetramethylsilane standard. All reactions described in Examples 1-25 were carried out under a positive pressure of nitrogen.

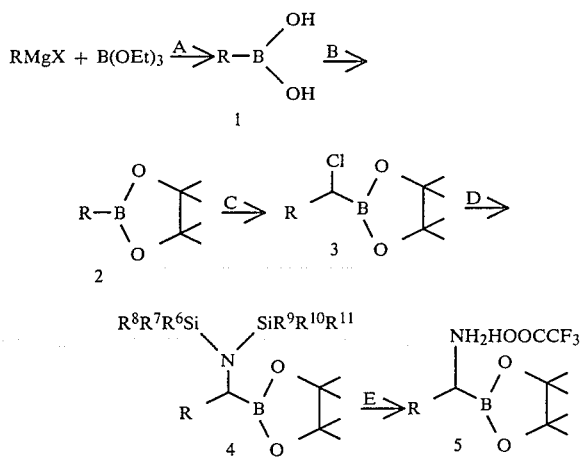

TABLE 1

| Summary of Examples 1-21 | | | | | |
|---|---|---|---|---|---|
| | Compound | | | | |
| R | 1 | 2 | 3 | 4 | 5 |
| —CH₃CH(CH₃)₂ | 1,2 | 1,2 | 3 | 4 | 5A,5B |
| —CH(CH₃)CH₂CH₃ | 6 | 6 | 7 | 8 | 9 |
| —CH(CH₃)₂ | 10 | 10 | 11 | 12 | 13 |
| —CH₂—C₆H₅ | 14 | 14 | 15 | 16 | 17 |
| —CH₃ | 18 | 18 | 19 | 20 | 21 |

EXAMPLE 1

Preparation of
4,4,5,5-tetramethyl-2-(2-methylpropyl)-1,3,2-dioxaborolane (2)

5.2 mL (4.626 g, 50 mmol) 1-chloro-2-methylpropane were added to a suspension of 1.459 g (60 mmol) magnesium in 20 mL anhydrous ether at 23°. A Grignard reaction was initiated by addition of a small (ca. 5 mg) crystal of iodine, and the resulting reaction mixture was stirred for 40 minutes. This solution was added dropwise to a flask containing 20 mL anhydrous ether, which was cooled in dry ice. Simultaneously, a solution of 8.76 g (10.2 mL, 60 mmol) triethylborate in 10 mL anhydrous ether was added slowly. The resulting mixture was stirred at −70° for 30 minutes, allowed to warm to 0°, then treated with 4 mL water.

The foregoing mixture was contacted with 13 mL of 20% sulfuric acid, and upon standing, an aqueous layer formed. The aqueous layer was separated, and extracted 3 times with 25 mL aliquots of ether. The residual organic layer and ether extracts were combined and evaporated to approximately one-half original volume. At this point, 20 mL water were added, evaporation was continued, and distillate at 70° was collected as an oil which solidified upon standing. This material and the residue from distillation were combined and extracted twice with 25 mL aliquots of ether. The resulting ether extracts were combined, dried over MgSO₄, and ether removed by distillation to provide 3.20 g of 2-methylpropylboronic acid as a hygroscopic solid (31.4 mmol, 62.8%), m.p. 90°-95°; ¹H NMR (90 MHz, C₃D₆O): δ0.9 (d, J=6.6 Hz, 2), 1.1 (d, J=6.6 Hz, 6), 2.1 (m, 1); MS: (m/z) 102.

A solution of 50.13 g (0.494 mol) of 2-methylpropylboronic acid in 300 mL of ether, prepared by a procedure substantially similar to the foregoing, was contacted with 112.63 g (0.494 mol) of pinacol hexahydrate and stirred for 24 hours. At the end of this period, the resulting reaction mixture was diluted with 500 mL of hexane. A top layer formed which was separated from the rest of the mixture and contacted with 18 mL of water. After stirring for 15 minutes, 9.52 g of a solid separated, which was removed by filtration. The remaining hexane layer was dried over Na₂SO₄ and residual solvent was removed by evaporation. The remaining material was then distilled using a 6" spinning band distillation column, to obtain 43.98 g (0.239 mol, 48.4%) of an oil, bp: 65°-72°/13 mm, ¹H NMR (90 MHz, CDCl₃): δ0.65 (d, J=6.6 Hz, 2), 0.93 (d, J=6.6 Hz, 6), 1.25 (s, 12), 1.86 (hep, J=6.6 Hz, 1); Anal. Calcd. for C₁₀H₂₁O₂B: C, 65.25; H, 11.50; B, 5.87; Found: C, 65.07, H, 11.52; B, 6.01.

EXAMPLE 2

Preparation of
4,4,5,5-tetramethyl-2-(2-methylpropyl)-1,3,2-dioxaborolane (2), (without isolation of 2-methylpropylboronic acid (1))

104.8 mL (92.6 g, 1 mol) 1-chloro-2-methylpropane was added to a suspension of 26.7 g (1.1 mol) magnesium in 200 mL anhydrous ether at about 23°. A Grignard reaction was initiated by addition of 0.5 mL ethylene bromide. When the reaction subsided, the resulting mixture was diluted with 400 mL anhydrous ether and stirred for 1 hour at ambient temperature. This Grignard reagent, and a solution of 170 mL (146 g, 1 mol) triethylborate in 530 mL anhydrous ether, were added simultaneously to a flask containing 500 mL anhydrous ether cooled to −78°. The rate of reagent addition was controlled to keep the reaction temperature below −68°. After addition was complete, the reaction mixture was allowed to warm to 23° C. and stirred for 16 hours. At this point, 250 mL of 40% (v/v) sulfuric acid was introduced while maintaining the temperature of the reaction mixture below 25°. After stirring for 16 hours, an organic layer was separated, and the remaining aqueous layer extracted 4 times with 200 mL aliquots of ether. The foregoing organic fractions were then combined and dried over MgSO₄. Solvent boiling below 60° was removed by distillation, leaving a liquid fraction of 143.18 g. This fraction was dissolved in 400 mL ether, treated with 228 g (1 mol) pinacol hexahydrate, and stirred for 16 hours. At this point, a top organic layer was separated and the remaining bottom layer extracted 5 times with 400 mL aliquots of n-hexane. The foregoing organic fractions were combined, dried over MgSO₄, and concentrated by solvent evaporation under reduced pressure. The residue was distilled using a 9" spinning band column, providing 93.83 q of a liquid, bp 76°-100°/24-20 mm. This material was dissolved in 500 mL n-hexane, to which 25 mL water were added. This mixture was stirred for 15 minutes, and the hexane layer was separated, concentrated by evaporation under reduced pressure, and then distilled using a 9" spinning band column, providing 43.73 g of a residual oil, bp 58°–80°/21 mm; $^1$H NMR (90 MHz, CDCl$_3$): δ0.73 (d, J=Hz, 2), 0.97 (d, J=6 Hz, 6), 1.2 (s, 12), 1.83 (m, 1).

EXAMPLE 3

Preparation of 2-(1-chloro-3-methylbutyl)-4,4,5,5-tetramethyl-1,3,2-dioxaborolane (3)

134 mL n-butyllithium (1.6 M, 0.221 mol) were added to 31.08 mL (22.43 g, 0.221 mol) ice-cold diisopropylamine containing 3 mL tetrahydrofuran. The resulting thick liquid was added to a solution of 33.98 g (0.185 mol) 4,4,5,5-tetramethyl-2-(2-methylpropyl)-1,3,2-dioxaborolane (2) in 165 mL glyme containing 17.72 mL (23.5 g, 0.277 mol) methylene chloride at −72°. When this addition was complete, the reaction mixture was stirred for 2 hours, diluted with 165 mL methylene chloride, and a white precipitate removed by filtration. The residue was washed twice with 25 mL portions of methylene chloride. The filtrates were combined, concentrated under reduced pressure, and then distilled from a 12" spinning band column, providing 16.96 g (0.087 mol, 39.46%) of an oil, bp 90°–93°/2.0 mm; $^1$H NMR (90 MHz, CDCl$_3$): δ0.90 (d, d, J=6, 3 Hz, 6), 1.3 (s, 12), 1.73 (m, 3), 3.45 (d, d, J=6 Hz, 1); Anal. Calcd. for C$_{11}$H$_{22}$O$_2$ClB: C, 56.81; H, 9.53; Cl, 15.24; B, 4.65; Found: C, 56.81; H, 9.46; Cl, 15.37; B, 4.53.

EXAMPLE 4

Preparation of 2-(1-[bis(trimethylsilyl)amino]-3-methylbutyl)-4,4,5,5-tetramethyl-1,3,2-dioxaborolane (4)

A solution of 4.55 g (5.95 mL, 0.028 mol) hexamethyldisilylhydrazide in 60 mL of tetrahydrofuran was cooled to −72° and treated with 17 mL of n-butyllithium (1.65, 0.282 mol). The resulting reaction mixture was warmed to 0°, then cooled to −78° and treated with 5.95 g (0.0256 mol) of 2-(1-chloro-3-methylbutyl)-4,4,5,5-tetramethyl-1,3,2-dioxaborolane (3). The resulting reaction mixture was warmed to room temperature and stirred for 72 hours. At the end of this period, solvent was removed under reduced pressure and the residue was distilled under vacuum, providing two fractions: 6.33 g, bp 120°–130°/0.05 mm; and 0.39 g, bp 180°–200°/0.025 mm (combined yield 73.6%). These two fractions showed the desired molecular ions in MS but were contaminated by traces of an unidentified material: $^1$H NMR (C$_3$D$_6$O, 80 MHz); δ0.15 (s, 18), 0.93 (d, d, J=6.6, 2.5 Hz, 6), 1.86 (two peaks, 12), 2.06 (m, 1). Material prepared in a substantially similar experiment provided an oil, (77.9% yield) bp: 76°–88°/0.1 mm, $^1$H NMR (CDCl$_3$, 360 MHz); 0.76 (d, d, J=7,6 Hz, 6), 1.115 (s, 12), 1.16 (8, J=7 Hz, 1), 1.435 (t, d, J=7,13 Hz, 1), 1.65 (hept. J=7 Hz, 1), 2.475 (t, J=8 Hz, 1); Anal. Calcd. for C$_{17}$H$_{40}$O$_2$NSi$_2$B: C, 57.12; H, 11.23; N, 3.92; Si, 15.71; B, 3.02; Found: C, 58.42; H, 11.05; N, 3.68; Si, 15.44; B, 2.99.

EXAMPLE 5

Preparation of 3-methyl-1-(4,4,5,5-tetramethyl-1,3,2-dioxaborolane-2-yl)-1-butamine, trifluoroacetic acid salt (5, R=CH$_2$CH(CH$_3$)$_2$, W=CF$_3$COO)

Procedure A

A solution of 0.050 g (0.00014 mol) of 2-(1-[bis(trimethylsilyl)amino]-3-methylbutyl)-4,45,5-tetramethyl-1,3,2-dioxaborolane (4, R=CH$_2$CH(CH$_3$)$_2$) in 2 mL of methylene chloride cooled to 0° was contacted with 32 μL (0.0479 g, 0.00042 mol) of trifluoroacetic acid and stirred for 2 hours. At the end of this period, the reaction mixture was evaporated, providing a solid; $^1$H NMR (CDCl$_3$, 360 MHz): δ0.91 (d, d, J=7.2 Hz, 6), 1.24 (s, 12), 1.57 (t, J=7 Hz, 2), 1.75 (hept, J=7 Hz, 1), 2.92 (br., 1), 6.9 (br., 3). MS: (M/z—CF$_3$COOH)=213. Material prepared in a substantially similar experiment produced a solid (68.5% yield); mp 153°–156°; $^1$H NMR as above. Anal. Calcd. for C$_{13}$H$_{25}$NO$_4$BF$_3$: C, 47.73; H, 7.70; C, 4.28; F, 17.42; B, 3.30; Found: C, 47.48; H, 7.44; N, 4.21; F, 17.59; B, 3.61.

Procedure B

A solution of 3.57 g (0.010 mol) of 2-(1-[bis(trimethylsilyl)amino]-3-methylbutyl)-4,4,5,5-tetramethyl-1,3,2-dioxaborolane (4, R=CH$_2$CH(CH$_3$)$_2$) in 20 mL of ether at 0° was treated with 2.38 mL (3.53 g, 0.031 mol) of trifluoroacetic acid. The resulting solution was stirred for 1 hour at 0° to obtain the desired material as a solid (2.06 g, 63.2% yield), mp 155°–157°.

EXAMPLE 6

Preparation of 2-(1-methylpropyl)-4,4,5,5-tetramethyl-1,3,2-dioxaborolane (2, R=CH(CH$_3$)CH$_2$CH$_3$)

This material was prepared by a procedure substantially similar to Example 2, as an oil (60.6% yield) bp: 72°–78°/20 mm, $^1$H NMR (90 MHz, CDCl$_3$); δ0.83–1.0 (br., 7), 1.23 (s, 12), 1.4–1.7 (br., 2); Anal. Calcd. for C$_{10}$H$_{21}$O$_2$B: C, 65.25; H, 11.50; B, 5.87; Found: C, 65.11; H, 11.36; B, 6.03; MS: (m/z) 184.

EXAMPLE 7

Preparation of 2-(1-chloro-2-methylbutyl)-4,4,5,5-tetramethyl-1,3,2-dioxaborolane (3, R=CH(CH$_3$)CH$_2$CH$_3$)

This compound was prepared substantially according to the procedure of Example 3, as an oil (yield 66.7%) bp: 80°–94°/1.0 mm, $^1$H NMR (360 MHz, CDCl$_3$): δ0.90 (t, d, J=7, 3 Hz, 3), 1.0 (d, d, J=7,6 Hz, 3), 1.29 (s, 12), 1.51 (m, 1), 1.65 (m, 1), 1.85 (m, 1), 3.3 (d, J=7 Hz, ½), 3.44 (d, J=5 Hz, ½); Anal. Calcd. for C$_{11}$H$_{22}$O$_2$BCl: C, 56.81; H, 9.53; B, 4.65; Cl, 15.25; Found: C, 56.52; H, 9.57; B, 4.56; Cl, 15.36; MS: (m/z) 232.

EXAMPLE 8

Preparation of 2-(1-[bis(trimethylsilyl)amino]-2-methylbutyl)-4,4,5,5-tetramethyl-1,3,2-dioxaborolane (4, R=CH(CH$_3$)C$_2$H$_5$)

This product was prepared by a procedure substantially similar to Example 4, in 67.7% yield: bp 100°–105°/0.1 mm; $^1$H NMR (90 MHz, CDCl$_3$): δ(0.1, s, 18), 0.88 (m, 6), 1.23 (s, 12), 1.43–2.3 (br., 4); Anal. Calcd. for C$_{17}$H$_{40}$NO$_2$BSi$_2$: C, 57.12; H, 11.28; N, 3.92; B, 3.02; Si, 15.7; Found: C, 56.83; H, 11.30; N, 3.81; B, 2.86; Si, 15.90; MS: (m/z) 357.

EXAMPLE 9

Preparation of 4,4,5,5-tetramethyl-α-(1-methylpropyl)-1,3,2-dioxaborolane-2-methanamine, trifluoroacetic acid salt (5, R=CH(CH$_3$)CH$_2$CH$_3$, W=CF$_3$COO)

This material was prepared by a procedure substantially similar to that described in Example 5, Procedure B, as a solid; (60.3% yield), mp 114°–116°; $^1$H NMR (CDCl$_3$, 360 MHz): δ0.91 (t, J=7 Hz, 3), 0.99 (t, J=7 Hz, 3), 1.10–1.385 (br., 1), 1.25 (s, 12), 1.5 (m, ½), 1.6 (m, ½), 1.78–1.9 (br., 1), 2.85 (t, J=5 Hz, 1), 7.5–7.85 (br., 3); Anal. Calcd. for C$_{13}$H$_{25}$NO$_4$BF$_3$: C, 47.73; H, 7.70; N, 4.28; B, 3,30; F, 17.42; Found: C, 47.91; H, 7.55; N, 4.28; B, 3,59; F, 17.39; MS: (m/z—CF$_3$COOH) 214.

EXAMPLE 10

Preparation of 2-(1-methylethyl)-4,4,5,5-tetramethyl-1,3,2-dioxaborolane (2, R=CH(CH$_3$)$_2$)

This material was prepared by a procedure substantially similar to Example 2 as an oil; (30.5% yield); bp 42°–58°/20 mm; $^1$H NMR (CDCl$_3$, 80 MHz); δ1.0 (s, 7), 1.23 (s, 12); Anal. Calcd. for C$_9$H$_{19}$O$_2$B: C, 63.36; H, 11.26; B, 6.37; Found: C, 63.62; H, 11.12; B, 6.22; MS:(m/z) 170.

EXAMPLE 11

Preparation of 2-(1-chloro-2-methylpropyl)-4,4,5,5-tetramethyl-1,3,2-dioxaborolane (3, R=CH(CH$_3$)$_2$)

This material was prepared by a procedure substantially similar to Example 3 as an oil: (70% yield); bp 74°–78°/1.0 mm; $^1$H NMR (CDCl$_3$, 80 MHz): δ1.03 (d, d, J=8,3 Hz, 6), 1.30 (s, 12), 2.06 (hept., J=6.6 Hz, 1), 3.23 (d, J=6.6, 1); Anal. Calcd. for C$_{10}$H$_{20}$O$_2$BCl: C, 54.96; H, 9.22; B, 4,95; Cl, 16.22; Found: C, 54.74; H, 9.33; B, 4.82; Cl, 15.05.

EXAMPLE 12

Preparation of 2-(1-[bis(trimethylsilyl)amino]-2-methyl)-4,4,5,5-tetramethyl-1,3,2-dioxaborolane (4, R=CH(CH$_3$)$_2$)

This material was prepared by a procedure substantially similar to that described in Example 4, providing the title compound as an oil; (79% yield) bp 75°–96°/0.75 mm; $^1$H NMR (CDCl$_3$ 360 MHz): δ0.125 (s, 18), 0.795 (t, J=6 Hz, 6), 1.24 (d, J=3 Hz, 12), 1.855 (m, 1), 2.95 (d, J=11 Hz, 1); Anal. Calcd. for C$_{16}$H$_{38}$NO$_2$BSi$_2$: C, 55.95; H, 11.15; N, 4.08; B, 3.15; Si, 16.35; Found: C, 56.12; H, 11.00; N, 4.19; B, 3.02; Si, 16.57; MS calcd. for C$_{16}$H$_{38}$NO$_2$BSi$_2$: 300.1987; obs. 300.1968.

EXAMPLE 13

Preparation of 4,4,5,5-tetramethyl-α-(1-methylethyl)-1,3,2-dioxaborolane-2-methanamine, trifluoroacetic acid salt (5, R=CH(CH$_3$)$_2$)

This material was prepared substantially as in Example 5, Procedure B, providing a solid; (51.0% yield); mp 108°–110°; $^1$H NMR (CDCl$_3$, 360 MHz): δ0.995 (t. J=8 Hz, 6), 1.26 (s, 12), 2.12 (m, 1), 2.75 (d, J=4 Hz, 1); Anal. Calcd. for C$_{12}$H$_{23}$NO$_4$BF$_3$: C, 46.03; H, 7.40; N, 4.47; B, 3.45; F, 18.20; Found: C, 46.12; H, 7.44; N, 4.50; B, 3.66; F, 18.49; MS: (m/z—CF$_3$COOH) 200.

EXAMPLE 14

Preparation of 4,4,5,5-tetramethyl-2-(phenylmethyl)-1,3,2-dioxaborolane (2 R=CH$_2$C$_6$H$_5$)

This material was prepared by a procedure substantially as described in Example 2, providing an oil; (38% yield); bp 128°–140°/20 mm; $^1$H NMR (CDCl$_3$, 80 MHz); δ1.20 (s, 12), 2.26 (s, 2), 7.16 (s, 5); Anal. Calcd. for C$_{13}$H$_{19}$O$_2$B: C, 71.59; H, 8.78; B, 4.96, Found: C, 71.46, H, 8,80; B, 4.71; MS: (m/z) 218.

EXAMPLE 15

Preparation of 2-(1-chloro-2-phenylethyl)-4,4,5,5-tetramethyl-1,3,2-dioxaborolane (3, R=CH$_2$C$_6$H$_5$)

This material was prepared by a procedure substantially similar to that described in Example 3, as an oil: (42.4% yield); bp 142°/0.1 mm; $^1$H NMR (CDCl$_3$, 360 MHz); δ1.20 (s, 12), 3.15 (m, 2), 3.55 (d, d, J=6.6 Hz, 1), 7.2 (s, 5); Anal. Calcd. for C$_{14}$H$_{20}$O$_2$BCl: C, 63.31; H, 7.56; B, 4.06; Cl, 13.30; Found: C, 63.29; H, 7.37; B, 4.05; Cl, 13.02; MS: (m/z) 266.

EXAMPLE 16

Preparation of 2-(1-[bis(trimethylsilyl)amino]-2-phenylethyl-4,4,5,5-tetramethyl-1,3,2-dioxaborolane (4, R=CH$_2$C$_6$H$_5$)

This material was prepared substantially as described in Example 4, providing the title compound; (75.8% yield); bp 114°–130°/0.005 mm; which solidified upon standing, mp 43°–44.5°. $^1$H NMR (CDCl$_3$, 360 MHz); δ0.11 (s, 18), 1.25 (s, 12), 2.66 (d, d, J=9,8 Hz, 1), 2.775 (t, J=6 Hz, 1), 3.05 (d, d, J=12,7 Hz, 1), 7.19 (m, 1), 7.26–6.28 (m, 4); Anal. Calcd. for C$_{20}$H$_{38}$NO$_2$Si$_2$B: C, 61.36; H, 9.78; N, 3.58; B, 2.76, Si, 14.35; Found: C, 61.16; H, 9.56; N, 3.61; B, 2.59; Si, 14.16; MS: (m/z—CH$_3$) 376.

EXAMPLE 17

Preparation of 4,4,5,5-tetramethyl-α-(phenylmethyl)-1,3,2-dioxoborolane-2-methanamine, trifluoroacetic acid salt (5, R=CH$_2$C$_6$H$_5$)

This material was prepared by a procedure substantially similar to that described in Example 5, procedure B, providing a solid; (20.8% yield); mp 109°–112°; $^1$H NMR (CDCl$_3$, 360 MHz): δ1.185 (two peaks, 12), 3.0–3.15 (br., 3), 7.2–7.35 (br., 5), 7.65–7.85 (br., 3); Anal. Calcd. for C$_{16}$H$_{23}$NO$_4$BF$_3$: C, 53.21; H, 6.42; N, 3.89; B, 2.99; F, 15.78; Found: C, 53.42; H, 6.43; N, 3.89; B, 3.07; F, 15.51; MS: (m/z—CF$_3$COO) 247.

EXAMPLE 18

Preparation of 2,4,4,5,5-pentamethyl-1,3,2-dioxaborolane (2, R=CH$_3$).

To a flask containing 500 mL ether at −72° was added a solution of 714 mL of methyllithium (1.4M, 1.0 mol), and, simultaneously, a solution of 170 mL of triethylborate (146 g, 1.0 mol) in 544 mL of ether. These reactants were added slowly, maintaining reaction temperature below −55°. After addition was complete, the reaction mixture was warmed to room temperature and stirred for 16 hours. At the end of this period, the reaction mixture was cooled in ice and treated with 250 mL of 40% sulfuric acid, maintaining mixture temperature below 25°. After stirring the resulting reaction product at room temperature for 16 hours, a top layer was separated, and the remaining bottom layer was extracted four times with 200 mL portions of n-hexane. The combined organic layers were dried over MgSO$_4$ and solvent was removed by evaporation at reduced pressure, providing 81.0 g of an oil. This oil was dissolved in 400 mL of ether, contacted with 200 g (0.884 mol) pinacol hexahydrate, and stirred for 16 hours. At the end of this period, the top layer was separated and the bottom layer extracted with 4 200 mL portions of n-hexane. The combined organic layers were stirred with 25 mL of water, providing a solid which was removed by filtration. The filtrate was concentrated under reduced pressure and then distilled, providing 51.11 g (36% yield) of the desired material as an oil; bp 42°–46°/30 mm; $^1$H NMR (CDCl$_3$, 80 MHz): δ0.23 (s, 3); 1.213 (s, 12); Anal. Calcd. for C$_7$H$_{15}$O$_2$B: C, 59.21; H, 10.65; B, 7.61; Found: C, 59.43; H, 10.53; B, 7.40; MS: Calcd. for C$_7$H$_{15}$O$_2$B, 142.1165; Found: 142.1161.

EXAMPLE 19

Preparation of 2-(1-chloroethyl)-4,4,5,5-tetramethyl-1,3,2-dioxaborolane (3, R=CH$_3$).

This material was prepared by a procedure substantially similar to that described in Example 3, providing an oil; (35.75% yield); bp 54°–56°/1.0 mm; $^1$H NMR (CDCl$_3$, 80 MHz): δ1.26 (s, 12), 1.53 (d, J=7 Hz, 3), 3.45 (q, J=8 Hz, 1); Anal. Calcd. for C$_8$H$_{16}$O$_2$BCl: C, 50.45; H, 8.46; B, 5.68; Cl, 18.61; Found: C, 51.18; H, 8.31; B, 5.17; Cl, 18.16; MS: (m/z) 190.

EXAMPLE 20

Preparation of 2-(1-[bis(trimethylsilyl)-amino]ethyl-4,4,5,5-tetramethyl-1,3,2-dioxaborolane (4, R=CH$_3$).

This material was prepared substantially as described in Example 4, affording an oil; (71.1% yield); bp 68°–74°/0.1 mm; $^1$H NMR (CDCl$_3$, 360 MHz) δ0.05 (s, 18), 1.1 (d, J=6.6 Hz, 3), 1.2 (s, 12), 2.6 (q, J=8 Hz, 1); Anal. Calcd. for C$_{14}$H$_{34}$NO$_2$Si$_2$B: C, 53.31, H, 10.82; N, 4.44; Si, 17.81; B, 3.43; Found: C, 53.35; H, 11.04; N, 4.64; Si, 17.64; B, 3.24. MS: (m/z) 315.

EXAMPLE 21

Preparation of α,4,4,5,5,pentamethyl-1,3,2-dioxoborolane-2-methanamine, trifluoroacetic acid salt (2, R=CH$_3$).

This material was prepared substantially as described in Example 6; providing a solid; (84.7% yield); mp 165°; $^1$H NMR (CDCl$_3$, 360 MHz); δ1.275 (s, 12), 1.40 (d, J=8 Hz, 3), 2.86–3.0 (br., 1), 7.75–7.95 (br., 3); Anal. Calcd. for C$_{10}$H$_{19}$NO$_4$BF$_3$: C, 42.13; H, 6.72; N, 4.91; B, 3.72; F, 19.99; Found: C, 41.66; H, 7.07; N, 5.06; B, 3.90; F, 19.76; MS: (m/z—CF$_3$COOH) 171.

EXAMPLE 22

Preparation of 2-(phenylmethyl)-1,3,2-dioxaborinane

This material was prepared by a procedure substantially similar to Example 2 by using 1,3-propanediol instead of pinacol hexahydrate, as an oil (32.3% yield); bp 103°–81°/2.2–1.3 mm; $^1$H NMR (CDCl$_3$, 80 MHz): δ1.8 (p, J=6 Hz, 2H), 2.2 (s, 2H), 3.95 (t, J=6 Hz, 4H), 7.2 (m, 5H); Anal. Calcd. for C$_{10}$H$_{13}$O$_2$B: C, 68.24; H, 7.44; B, 6.14; Found: C, 68.05; H, 7.26; B, 5.97; MS: (m/z) 176.0997.

EXAMPLE 23

Preparation of 2-(1-chloro-2-phenylethyl)-1,3,2-dioxaborinane

This compound was prepared by a procedure substantially similar to Example 3, as an oil; (54% yield) bp 109°–118°/0.6–0.3 mm; $^1$H NMR (CDCl$_3$, 80 MHz) δ2.0 (p, J=6 Hz, 2H); 3.1 (m, 2H); 3.5 (m, 1H); 4.1 (t, J=6 Hz, 4H); 7.35 (m, 5H); Anal. Calcd. for C$_{11}$H$_{14}$O$_2$BCl: C, 58.85, H, 6.29; B, 4.82; Cl, 15.79; Found: C, 61.46; H, 6.29; B, 4.56; Cl, 14.75; MS: (m/z) 224.

EXAMPLE 24

Preparation of 2-(1-[bis(trimethylsilyl)-amino]-2-phenylethyl)-1,3,2-dioxaborinane This compound was prepared by a procedure substantially similar to Example 4, as an oil; (62% yield) bp 134°–131°/0.4–0.25 mm; $^1$H NMR (CDCl$_3$, 80 MHz): δ0 (s, 18); 1.86 (p, J=6 Hz, 2H); 2.7 (m, 3); 3.95 (t, J=6 Hz, 4); 7.2 (s, 5H). A sample of this material was distilled to obtain an oil; bp. 130°/0.18 mm; Anal. Calcd. for C$_{17}$H$_{32}$NO$_2$BSi$_2$: C, 58.43; H, 9.25; N, 4.01; B, 3.09; Si, 16.08; Found: C, 57.22; H, 9.59; N, 3.59; B, 2.78; Si, 13.94; MS: (m/z—2H) 334.1830.

EXAMPLE 25

Preparation of α-(1,3,2-dioxaborinan-2-yl)benzeneethanamine, trifluoroacetic acid salt This material was prepared by a procedure substantially similar to that described in Example 5, procedure B, as a solid; (87.5% yield); mp 85°–95°; $^1$H NMR (CDCl$_3$, 80 MHz): δ1.80 (p, J=6 Hz, 2H), 2.9 (s, 3H), 3.8 (t, J=5 Hz, 4H), 7.1 (s, 5H), 7.4 (br., 3H); Anal. Calcd. for C$_{13}$H$_{17}$NO$_4$BF$_3$: C, 48.93; H, 5.37; N, 4.39; B, 3.39, F, 17.86; Found: C, 47.53; H, 5.44; N, 4.47; B, 3.65, F, 18.82; MS: (m/z CF$_3$COOH) 205.

UTILITY EXAMPLES

Selected compounds 5 of the invention were tested for ability to inhibit the following aminopeptidases:
1. Leucine aminopeptidase (cytosolic) (LAPC) from hog kidney;
2. Leucine aminopeptidase (Microsomal) (LAPM) from hog kidney; and
3. Human enkephalin-degrading aminopeptidase (HEDA) from human serum. (See Colletti-Previero, Biochem. Biophys. Acta 657:122 (1981)).

In the experiments described in Examples 26, 27 and 30, below, IC$_{50}$ values for the foregoing enzymes were determined for illustrative compounds 5. An IC$_{50}$ value represents an approximation of the concentration of enzyme inhibitor required to inhibit enzyme activity by fifty percent. These values represent acceptable approximations of the inhibition constant K$_I$, the dissociation constant in the following equation:

$$E + I \rightleftharpoons EI$$

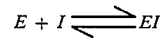

where [E] is the concentration of enzyme, [I] is the concentration of inhibitor and [EI] is the concentration of enzyme/inhibitor complex.

Determination of $IC_{50}$ values for LAPC and LAPM was accomplished by spectrophotometrically or fluorometrically following the rate of formation of p-nitroaniline or β-naphthylamine from hydrolysis of (L)-leucine-p-nitroanilide or (L)-leucine-β-napthylamide, respectively, in the presence of active enzyme. $IC_{50}$ values for HEDA were determined by monitoring, via high pressure liquid chromatography, the formation of destyrenkephalin from leu-enkephalin. $IC_{50}$ values for illustrative compounds within the scope of the present invention are set forth in Table 2, below:

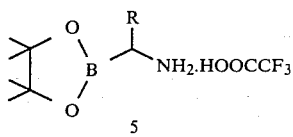

TABLE 2

| | $IC_{50}$ values (M) for selected α-aminoboronic acids 5 | | |
|---|---|---|---|
| | | $IC_{50}$ | |
| R | LAPM | LAPC | HEDA |
| —$CH_2C_6H_5$ | $2 \times 10^{-10}$ | $1 \times 10^{-8}$ | $5.2 \times 10^{-9}$ |
| —$CH_2CH(CH_3)_2$ | $1.2 \times 10^{-9}$ | $1.5 \times 10^{-7}$ | $7.4 \times 10^{-9}$ |
| —$CH(CH_3)C_2H_5$ | $2.2 \times 10^{-9}$ | $3 \times 10^{-8}$ | $4.1 \times 10^{-8}$ |
| —$CH(CH_3)_2$ | $2.15 \times 10^{-9}$ | $7 \times 10^{-8}$ | $4.2 \times 10^{-8}$ |
| —$CH_3$ | $6.4 \times 10^{-9}$ | $3 \times 10^{-5}$ | $7.1 \times 10^{-8}$ |

Due to the very low concentrations needed to inhibit LAPM and LAPC, the compounds 5 of the present invention can be used as titrants to directly determine enzyme activity present in a solution. In these experiments, detailed in Examples 28 and 29, a sample containing active enzyme in solution was treated with varying amounts of inhibitors 5 and allowed to reach an equilibrium in storage at 0°–5° for 16–40 hours. Longer periods can also be employed. After storage, an aliquot of the enzyme/inhibitor solution is tested for residual enzyme activity as previously described. A plot of inhibitor concentration (ordinate) versus the rate of residual activity (abscissa) provides a straight line which, when extrapolated to zero residual activity, indicates the concentrations of inhibitor equal to the effective concentration of enzyme active sites present in the sample tested. This titration method can be employed where $IC_{50}$ values are at least 10 times smaller than the active site concentration to be determined.

EXAMPLE 26

Determination of $IC_{50}$ value for compounds 5 with leucine aminopeptidase (microsomal) (LAPM)

Assay mixtures were prepared containing 0.613 μg LAPM, 10 μg/mL bovine serum albumin (BSA). 0.1M phosphate buffer, pH 7.2, in a total volume of 2.7 mL. Measured amounts of compounds 5 to be tested for inhibitory activity were added in additional 0.1M phosphate buffer to a total volume of 3 mL. After 72 hours at 0°–5°, 1 mL of the enzyme/inhibitor mixture was treated with 4 μL of 0.2M (L)-leucine-β-napthylamide in dimethylsulfoxide, and the rate of increase of fluorescence at 410 nm, while exciting at 310 nm. was measured. Control experiments were performed identically, except no inhibitor was present. The concentration of the selected compound 5 observed to decrease reaction rates by one-half was used to determine the value of $IC_{50}$ for each compound. This was accomplished by subtracting one-half the concentration of enzyme present in the sample mixtures ($1.6 \times 10_{-9}$M) from the inhibitor concentration observed to decrease reaction rates by one-half. The results of these experiments are set forth in Table 2, above.

EXAMPLE 27

Determination of $IC_{50}$ values for compounds 5 with Leucine aminopeptidase (cytosolic)(LAPC).

Assay mixtures were prepared, containing $10 \times 10^{-8}$M LAPC, 1 mg/mL BSA, 0.025M $MgCl_2$ and 0.01M tris-HCl buffer, pH 8.5, in a total volume of 2.7 mL. Varying amounts of selected compounds 5, dissolved in the same buffer, were added to make a final volume of 3.0 mL. After storage for 112 hours at 0°–5°, 1 mL of this mixture was treated with 25 μL of a 0.1M (L)-leucine-p-nitroanilide in dimethylsulfoxide, and the rate of increase of absorption at 405 nm was measured. $IC_{50}$ values were calculated as in Example 26, above. The results of these experiments are set forth in Table 2.

EXAMPLE 28

Determination of LAPM Active Site Concentration

Assay mixtures containing 5 μL of stock LAPM solution (0.057 mg/mL), 1 mg/mL BSA, and varying amounts of a $3 \times 10^{-8}$M solution of compound 5 (R=$CHCH_2(CH_3)_2$) in 0.1M phosphate buffer, pH 7.2, were preapred in a total volume of 100 μL and incubated at 0°–5° for 16 hours. At the end of this period, 80 μL of this mixture were diluted to 1 mL with phosphate buffer containing 4 μL of 0.2M (L)-leucine-β-naphthylamide in dimethylsulfoxide, and the rate of increase in fluorescence at 400 nm by irradiation at 310 nm was measured. From this rate, and using the fluorescence shown by a standard solution of β-naphthylamine, the rate of the reaction was calculated. A plot of the rate of the reaction on y-axis and the concentration of the inhibitor in the incubation mixture on x-axis was made. Extrapolating a straight line fitted to the plotted points to rate=0 indicated an enzyme active site concentration of $40 \times 10^{-9}$M.

EXAMPLE 29

Determination of LAPC Active Site Concentration

Assay mixtures containing 20 μL of an enzyme stock solution, 0.5M Tris-HCl (pH=8.5), 0.025M $MgCl_2$ and varying amounts of compound 5 (R=$CH_2C_6H_5$) were prepared in a total volume per assay of 200 μL. Each assay mixture was incubated at 23° for 4 hours, and 40 μL of each were added to 1.98 mL tris-HCl, pH=8.5, containing 2.5 mM (L)-leucine-p-nitroanilide. Rates of increase in absorption at 405 nm were determined. Rates were plotted versus inhibitor concentration as described in Example 28. Extrapolating a straight line fitted to the plotted points to rate=0 indicated an enzyme active site concentration of $10^{-6}$M.

EXAMPLE 30

Determination of $IC_{50}$ values for compounds 5 with human enkephalindegrading aminopeptidase Sample mixtures containing 2 mg/mL HEDA, 2 mM phosphate buffer, pH 7.8, and varying amounts of the inhibitor to be tested, in a total volume of 135 μL, were incubated at 37° for 2 hours. At this point, 15 µL of a 10 mM solution of leu-enkephalin, acetic acid salt in 2 mM phosphate buffer, pH 7.8, were added to each sample mixture. From each sample, b 25 µL aliquots were taken at 30 minute intervals and added to 125 µL 0.05M phosphate buffer, pH 2.5, and the resulting mixture injected onto a Du Pont Zorbax ® ODS reverse-phase high pressure liquid chromatography column, mounted on a Hewlett-Packard 1084B high pressure liquid chromatograph. Samples were eluted with a 1:4 (V/V) mixture of 0.05M phospate buffer, pH 2.5, and acetonitrile at 2 mL/min. Detection was by ultraviolet absorption at 215 nm. A ratio of a peak corresponding to (destyr)-enkephalin at about 2.9 nm and a peak corresponding to leu-enkephalin at about 3.9 min. indicated reaction progress. The rate of increase of this ratio corresponded to the rate of enzyme hydrolysis of substrate leu-enkephalin. Results, calculated substantially as described in Examples 26 and 27, are tabulated in Table 2.

INSECTICIDAL UTILITY

Suprisingly, certain intermediates 2 and 3 of the invention exhibit insecticidal activity at an application rate of 5 lb./acre, as summarized below:

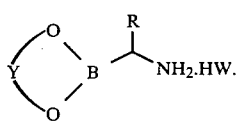

| R | | |
|---|---|---|
| —CH₃ | Ant Feeding, 31% control | — |
| —CH₃CH(CH₃)₂ | Leaf Hopper, 50% control | Mite, 64% control |
| —CH(CH₃)C₂H₅ | Bollworm, 20% control | Bean aphid 39% control |
| —CHC₆H₅ | Mite, 70% control | Bean aphid 48% control |

What is claimed is:
1. A compound of the formula

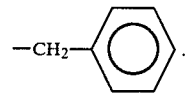

wherein
R is alkyl or —CH₂R¹;
R¹ is —XR², aryl, or aryl substituted with one or more alkyl groups;
R² is —H, alkyl, or —SiR³R⁴R⁵;
R³, R⁴ and R⁵ are independently alkyl, aryl or aryl substituted with one or more alkoxy groups;
X is O or S;
Y is a moiety derived from a dihydroxy compound comprising at least two hydroxy groups separated by at least two connecting atoms in a chain or ring, said chain or ring comprising carbon atoms and, optionally, a heteroatom which can be N, S, or O; and
HW is a mineral acid, sulfonic acid, alkanoic acid or a perfluoroalkanoic acid.
2. A compound according to claim 1 wherein Y is derived from pinacol, perfluoropinacol, pinanediol, ethylene glycol, diethylene glycol, catachol, 1,2-cyclohexanediol, 1,3-propanediol, 2,3-butanediol, 1,4-butanediol, or diethanolamine.
3. A compound according to claim 2 wherein HW is HCl, HBr, HI, a sulfonic acid, alkanoic acid, or perfluoroalkanoic acid.
4. A compound according to claim 3 wherein R is —CH₃, —CH(CH₃)₂, —CH₂CH₂(CH₃)₂, —CH(CH₃)C₂H₅, or

5. A compound according to claim 4 wherein Y is $(CH_3)_2\overset{|}{C}-\overset{|}{C}(CH_3)_2$, —CH₂CH₂—, $(CF_3)_2\overset{|}{C}-\overset{|}{C}(CF_3)_2$, or —(CH₂)₂NH(CH₂)₂—.
6. A compound according to claim 5 wherein HW is CF₃CO₂H, CH₃CO₂H, HCl or HBr.
7. A compound according to claim 6 wherein R is —CH(CH₃)C₂H₅ or

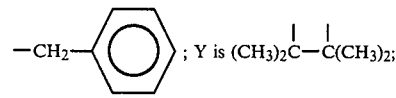

; Y is $(CH_3)_2\overset{|}{C}-\overset{|}{C}(CH_3)_2$;

and HW is CF₃CO₂H.
8. A compound according to claim 6 where R is

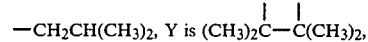

and HW is CF₃CO₂H.
9. A compound of formula

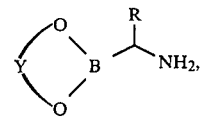

wherein
R and Y are as defined in claim 1, provided that where Y is —CH₂CH₂—, R cannot be

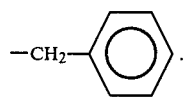

10. A compound according to claim 9, wherein Y is derived from pinacol, perfluoropinacol, pinanediol, ethylene glycol, diethylene glycol, catachol, 1,2-cyclohexanediol, 1,3-propanediol, 2,3-butanediol, 1,4-butanediol, or diethanolamine.
11. A compound according to claim 10 wherein R is —CH₃, —CH(CH₃)₂, —CH₂CH₂(CH₃)₂, —CH(CH₃)C₂H₅, or

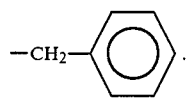

12. A compound according to claim 11, wherein Y is

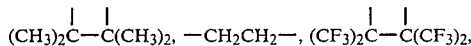

or —(CH$_2$)$_2$NH(CH$_2$)$_2$—.

13. A compound of the formula

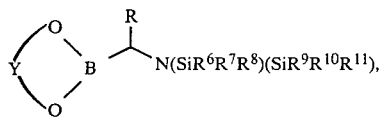

wherein
R and Y are as defined in claim 1,
R$^6$ through R$^{11}$ are independently alkyl, aralkyl, aryl, or substituted aryl, provided that, where R$^6$ through R$^{11}$ are each —CH$_3$ and Y is —CH$_2$CH$_2$— or

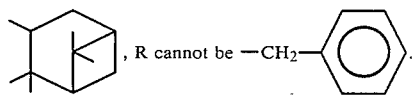

14. A compound according to claim 13, wherein Y is derived fro pinacol, perfluoropinacol, pinanediol, ethylene glycol, diethylene glycol, catachol, 1,2-cyclohexanediol, 1,3-propanediol, 2,3-butanediol, 1,4-butanediol, or diethanolamine.

15. A compound according to claim 14 wherein R is —CH$_3$, —CH(CH$_3$)$_2$, —CH$_2$CH$_2$(CH$_3$)$_2$, —CH(CH$_3$)C$_2$H$_5$, or

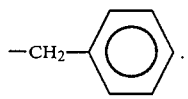

16. A compound according to claim 15, wherein Y is

or —(CH$_2$)$_2$NH(CH$_2$)$_2$—.

17. A compound of the formula

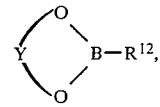

wherein
R$^{12}$ is lower alkyl or benzyl andd Y is as defined in claim 1; provided that, where Y is —CH$_2$CH$_2$— or

R$^{12}$ cannot be benzyl.

18. A compound of the formula

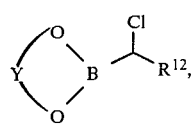

wherein
R$^{12}$ is lower alkyl or benzyl; and
Y is as defined in claim 1; provided that, where Y is —CH$_2$CH$_2$— or

R$^{13}$ cannot be benzyl.

19. A pharmaceutical composition for potentiating analgesia in a mammal comprising an effective amount of a compound of claim 1 and a pharmaceutically acceptable carrier.

20. A method of potentiating analgesia in a mammal comprising administering a composition of claim 19.

21. A pharmaceutical composition for potentiating analgesia in a mammal comprising an effective amount of a compound of claim 9 and a pharmaceutically acceptable carrier.

22. A method of potentiating analgesia in a mammal comprising administering a composition of claim 21.

* * * * *